(12) United States Patent
Greiner-Perth et al.

(10) Patent No.: US 6,427,878 B1
(45) Date of Patent: Aug. 6, 2002

(54) APPARATUS FOR THE DISCHARGE OF AN ATOMIZED LIQUID MEDIUM IN PARTIAL STROKES OF DIFFERENT LENGTH

(75) Inventors: Juergen Greiner-Perth, Gottmadingen; Hans Merk, Gaienhofen-Horn, both of (DE)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 0 days.

(21) Appl. No.: 09/652,400

(22) Filed: Aug. 31, 2000

(30) Foreign Application Priority Data

Sep. 15, 1999 (DE) .......................................... 199 44 211

(51) Int. Cl.[7] .............................................. A61M 5/315
(52) U.S. Cl. ........................................ 222/391; 604/209
(58) Field of Search .......................... 222/391; 604/309, 604/210, 224

(56) References Cited

U.S. PATENT DOCUMENTS

| | | | | |
|---|---|---|---|---|
| 3,949,748 A | * | 4/1976 | Malmin | 604/210 X |
| 4,625,981 A | | 12/1986 | Marchionne | |
| 4,962,868 A | * | 10/1990 | Borchard | 604/210 X |
| 5,092,842 A | * | 3/1992 | Bechtold et al. | 604/209 X |
| 5,284,132 A | * | 2/1994 | Geier | 604/224 X |
| 5,350,365 A | * | 9/1994 | De Godoy Moreira | 604/209 |
| 5,496,293 A | * | 3/1996 | Huggenberger | 604/609 |
| 5,501,373 A | | 3/1996 | Galli | |
| 5,662,098 A | | 9/1997 | Yoshida | |

FOREIGN PATENT DOCUMENTS

| | | |
|---|---|---|
| CH | 641 736 A5 | 3/1984 |
| DE | 40 08 068 A1 | 9/1991 |
| DE | 40 16 126 A1 | 10/1991 |
| DE | 197 23 133 A1 | 12/1998 |
| DE | 197 49 514 A1 | 5/1999 |
| EP | 0 334 349 A1 | 9/1989 |
| EP | 0 711 571 A1 | 5/1996 |
| FR | 2 625 981 | 7/1989 |
| GB | 2 316 451 A | 2/1998 |
| WO | WO 93/02804 | 2/1993 |
| WO | WO 97/06842 | 2/1997 |

* cited by examiner

Primary Examiner—Kenneth Bomberg
(74) Attorney, Agent, or Firm—Quarles & Brady LLP

(57) ABSTRACT

The invention relates to an apparatus for the atomized discharge of a liquid medium. The apparatus can be operated with one hand for the discharge of a liquid medium in partial strokes that are successively performed and not unintentionally interrupted. The apparatus has an operating trigger to engage the ram, which operates the piston that is displaceable in the spray cylinder, the operating path of the operating trigger being so limited between an operating starting position and end position that the resulting discharge stroke of the piston may vary for successive partial discharges of the stored medium.

22 Claims, 3 Drawing Sheets

APPARATUS FOR THE DISCHARGE OF AN ATOMIZED LIQUID MEDIUM IN PARTIAL STROKES OF DIFFERENT LENGTH

FIELD OF APPLICATION AND PRIOR ART

FR 88 00 454 discloses an apparatus for the optionally atomized discharge of an in particular liquid medium, in which the medium is stored in a spray cylinder and the medium can be discharged by means of a discharge channel. For this purpose the spray cylinder contains a piston, which can be actuated by a ram, the piston being manually operable. The manual operation of the ram takes place by means of an operating trigger or pusher, which is guided in a casing, which also receives the spray cylinder. On the casing and on the operating trigger are provided guide means, which limit the operation of the operating trigger in the axial direction of the spray cylinder, so that the overall stroke of the ram in the spray cylinder is subdivided into several, clearly defined partial strokes. In order to be able to perform the next partial stroke at the end of a first partial stroke, it is necessary to twist the operating trigger with respect to the spray cylinder or the casing in which the spray cylinder is located.

EP 334 349 A1 discloses an apparatus for the discharge of a medium in which the ram of a spray cylinder is operated by means of an operating trigger. The operating trigger is guided in a casing serving to receive the spray cylinder. On the casing are formed guide cams, which are guided in a slide path shaped onto the operating trigger. The slide path is shaped in such a way that the operating path of the operating trigger is subdivided into several partial strokes. This takes place either in that the slide path is stepped, so that between two partial strokes of the operating trigger it is necessary to twist the operating trigger with respect to the casing, or in that the slide path has overpressable stop or dwell points, which keep a cam guided in the slide path in an end position of a partial stroke until the operating force exceeds a retaining force. In the latter case the slide path can also be linear.

In apparatuses for the discharge of media in which it is necessary to twist the operating trigger with respect to the casing in order to perform successive partial strokes, it is disadvantageous that there is no possibility of a one-hand operation. For twisting the operating trigger with respect to the casing it is necessary to hold the apparatus with both hands. However, stepped guides have the advantage that an accidental successive performance of two partial strokes in a single movement is impossible. The construction with a linear slide path and dwell points overpressable by overcoming a retaining force for subdividing the discharge of the medium into several partial strokes admittedly gives the possibility of one-hand-operation, but the risk arises that unintentionally several partial strokes are successively performed in an uninterrupted operation.

PROBLEM AND SOLUTION

The problem of the invention is to provide an apparatus operable with one hand for the discharge of a liquid medium in which it is ensured that partial strokes are not unintentionally performed in uninterrupted succession.

This problem is solved by apparatuses according to the independent claims.

According to a first apparatus according to the invention an operating trigger acts on the ram, which operates the piston displaceable in the spray cylinder, the operating path of the operating trigger being so limited between an operation starting and end position that the resulting piston discharge stroke corresponds to the amount required for the discharge of a partial charge.

According to advantageous developments of the apparatus a return or restoring spring is provided for returning the operating trigger from the operation end position into the operation starting position. On the ram acting on the spray cylinder piston are shaped drivers, which solely in the direction of the discharge stroke provide a non-positive connection between the operating trigger and the ram. In addition, according to an advantageous development, on the ram can also be shaped locking means, which in the operation starting position engage on a locking edge and which can be overpressed by overcoming a minimum operating force of the operating trigger. It can be particularly advantageous to construct the drivers in such a way that the drivers of one discharge stroke serve as the locking means for a following discharge stroke.

According to a development of the invention the drivers are constructed as thickenings of the ram and it is particularly advantageous to construct the ram section constructed as a driver in the form of a frustum, the imaginary apex of the frustum being located in the direction of the spray cylinder piston. Further advantageous developments of the apparatus for discharging a medium can be gathered from the further subclaims.

A second apparatus for the discharge of a medium is also formed by a spray cylinder in which is located a piston operable by means of a ram. For this purpose a sliding shoe engages on the ram in an area outside the spray cylinder and the ram has at least one collar. In the operation end position of an operating stroke corresponding to the discharge of a partial charge the collar is engaged with the sliding shoe.

According to an advantageous development of this embodiment the sliding shoe is supported on the spray cylinder in the operation end position. A further advantageous development comprises the collar being formed by a diameter enlargement of the ram. Further advantageous developments of this embodiment deal with the articulation of the sliding shoe.

Further subclaims deal with advantageous developments of both embodiments.

These and further features can be gathered from the claims, description and drawings and the individual features, either singly or in the form of sub-combinations can be implemented in an embodiment of the invention and in other fields and can represent advantageous, independently protectable constructions for which protection is hereby claimed. The subdivision of the application into individual sections and the subtitles in no way restrict the general validity of the statements made thereunder.

BRIEF DESCRIPTION OF THE DRAWINGS

Embodiments of the invention are described in greater detail hereinafter relative to the attached drawings, wherein show.

DESCRIPTION OF THE EMBODIMENTS ACCORDING TO FIGS. 1 AND 2

Figure 1:
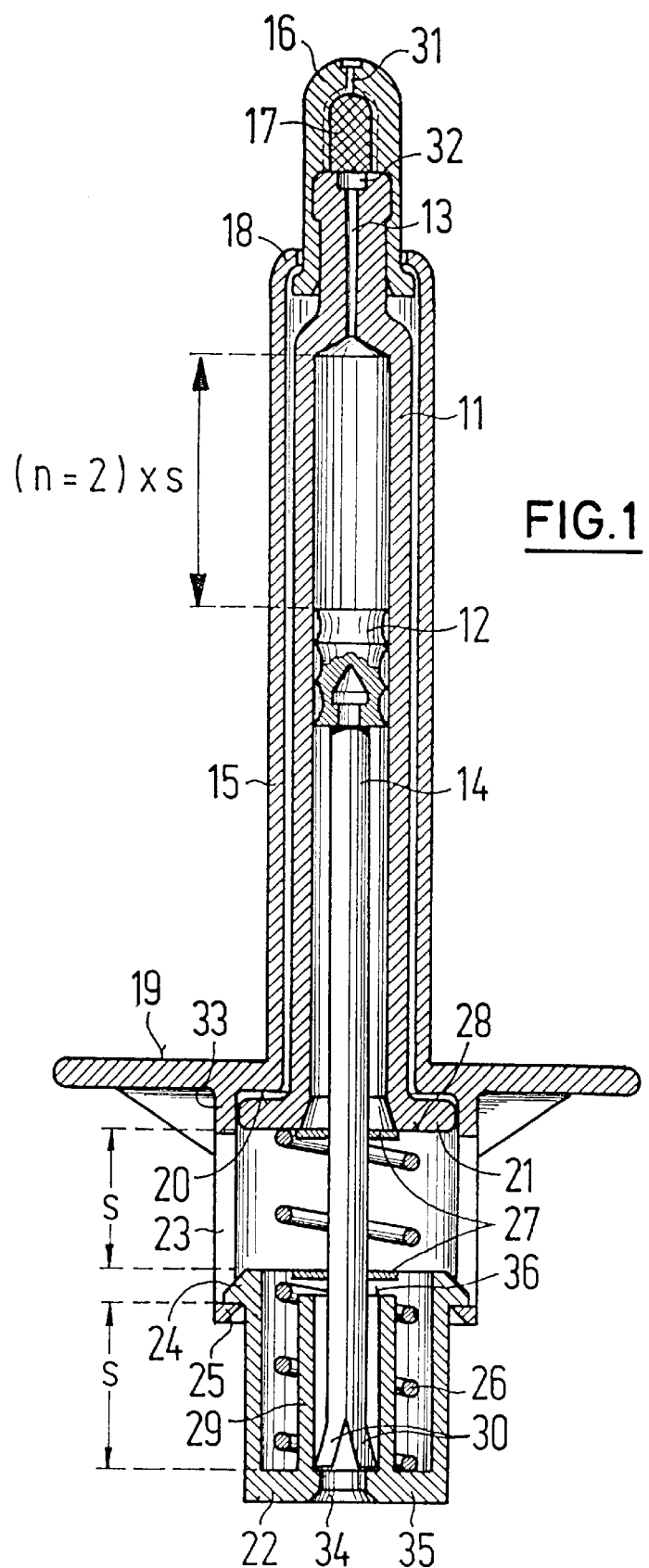
FIG. 1 A sectional representation of a first embodiment of an apparatus in which the operating path of the operating trigger is limited to the stroke needed for the discharge of a partial charge.

FIG. 1 is a cross-section through an apparatus for the optionally atomized discharge of an in particular liquid medium. The medium to be discharged is located in the spray cylinder 11, in which is installed the piston 12 displaceable in the axial direction of the spray cylinder. The spray cylinder 11 issues into the discharge channel 13 through which the medium is discharged if, by means of the ram 14 as a result of a manual operation, the piston 12 in the spray cylinder 11 is moved in the direction of the discharge channel 13.

On the side of the discharge channel 13 a cap 16 is held via the connection edge 18 of the casing 15 and into it issues the discharge channel 13 of the spray cylinder 11. On its front tip remote from the discharge channel 13 the cap 16 has a nozzle 31 as an outlet port for the medium to be discharged. Between cap 16 and opening 32 of the discharge channel 13 is located the sealing element 17. The sealing element 17 constitutes a hermetic seal between the nozzle 31 and the opening 32 of the discharge channel 13 until the apparatus is operated for the first time. This reliably ensures the prevention of any infection or an air access to the medium to be discharged stored in the spray cylinder 11. This is particularly important if the medium to be discharged is a medicine to be stored in sterile manner. This could e.g. be in the form of medicaments against migraine or inoculating serums or vaccines, which are administered to the patient via the nasal mucosa, because they can be particularly well absorbed there by the patient.

The sealing element 17 can either be constructed in such a way that during the first operation, i.e. the first partial stroke, it irreversibly frees a channel between the opening 32 of the discharge channel 13 and the nozzle 31 of the cap 16. It is also possible to construct the sealing element 17, e.g. from an elastic material, in such a way that the channel between the opening 32 and nozzle 31 in each case only opens for the duration of a partial stroke and subsequently immediately closes again. The latter construction has the advantage that no air can pass via the nozzle 31 to the discharge channel 13.

At the end opposite to the discharge channel 13 the spray cylinder 11 has a widening 21, which is supported on the contact surface 20 of the casing 15. The contact surface 20 is formed by a radial widening of the casing 15, which simultaneously advantageously serves as a finger bearing surface 19 for supporting the casing 15 in the hand of the user during operation of the apparatus. This simultaneously ensures that prior to the first partial stroke, considered from the discharge channel 13, the finger bearing surface 19 is located behind the piston 12, which advantageously ensures a stable, operation-reliable handling of the apparatus.

Surrounding the widening 21 of the spray cylinder 11 the shaft 33 of the casing 15 projects down rearwardly. The shaft 33 contains guide slots 23 in which engage detents 24, which are shaped onto the operating trigger 22. The shaft 33 also has at its rear end an end ring 25 terminating the guide slots 23. The outer contour of the operating trigger 22 is cup-shaped and is axially displaceably held by its detents 24 in the shaft 33. The possible operating path s of the operating trigger 22 between its represented operation start position and the operation end position is fixed by the free length of the guide slots 23 in the shaft 33 of the casing 15. In the operation end position the leading edge of the operating trigger 22 engages on the widening 21 of the spray cylinder 11.

Between the widening 21 of the spray cylinder 11 and the operating trigger 22 is provided the restoring or return spring 26, which has two functions. As a result of its biasing it produces a force acting between the operating trigger 22 and the spray cylinder 11, so that on the one hand the operating trigger 22 of the casing 15 is held in its operation starting position and on the other the spray cylinder 11 is secured against axial displacement in the casing 15.

The ram 14 extends from the piston 12 to the base surface 35 of the operating trigger 22. On the ram 14 are shaped locking means 27, which are in each case spaced from one another by the operating path s and which in the operation starting position of a partial stroke engage on the locking edge 28, which is preferably formed by the widening 21 of the spray cylinder 11. In conjunction with the locking edge 28, the locking means 27 form a pressure point opposing the operation of the operating trigger 22, which preferably ensures that during each operation of the operating trigger 22 such an operating force is applied to it that it is always brought in a continuous, uninterrupted operation over its entire operating path from the operation starting position to the operation end position. At its rear end, remote from the piston 12, the ram 14 has a driver 30, which prior to the initial operation is in engagement with the inside of the base surface 35. As a result of a notch the driver 30 has a radial bias or pretension, which radially urges it in the direction of the inner sleeve 29, shaped onto the base surface 35 of the operating trigger 22 and having a length corresponding to the operating path s.

The number n of partial strokes in which is discharged the medium stored in the spray cylinder 11 is two in the apparatus shown. Thus, the volume available for the medium in the spray cylinder is predetermined. The volume is determined from the internal diameter of the spray cylinder 11 and the displacement length of the piston 12 between its starting position (as shown) and its end position, when displaced by the predetermined number n of operating paths s in the direction of the discharge channel 13. It is also possible for the individual operating elements to have different operating paths. This is possible via the distance of the driver 30 from the base surface 35 before the first operating stroke and from the inner sleeve 36 before the second operating stroke. In order to ensure identical discharge volumes, it is particularly possible for the first partial stroke to be larger than the second partial stroke, because during the first partial stroke an idle path is necessary for opening the sealing element 17. In the represented example this can be brought about in that the inner sleeve 29 is longer by a predetermined amount than the operating path s of the operating trigger 29 during the first partial stroke.

If the operating trigger 22 is now operated, which generally takes place in that the trigger 22 on the outside of the base surface 35 is subject to a minimum force as a result of the thumb of the user, then the operating trigger 22 is moved into the operation end position from the operation starting position by the operating path s in the manner shown. There is an action on the ram 14 by means of the driver 30 and is moved by the same operating path s, so that the piston 12 is moved in the spray cylinder 11 by the operating path s. A medium volume corresponding to the displaced volume is discharged from the spray cylinder 11 through the discharge channel 13 via the cap with the nozzle 31 and is normally atomized by said nozzle 31. In addition to its bias, the return spring 26 is further tensioned by shortening its length. The operating trigger 22 is released at the end of the operation. As a result of the force of the return spring 26 applied between the spray cylinder 11 and the operating trigger 22, the latter is brought back into the operation starting position. Through the shaping of the piston 12 and the action of the locking means 27, which are pressed into the spray cylinder 11, it can be ensured that there is no moving back of the ram 14 together with the operating trigger 22. Instead the drivers 30 slide along the inner sleeve 29. As soon as the operating trigger 22 again reaches the operation starting position, which is defined by the end ring 25, the drivers 30 leave the inner sleeve 29 and engage with the inner sleeve upper edge 36. During the next operation the operating force acting on the operating trigger 22 is transferred by means of the inner sleeve 29 to the drivers 30 of the ram 14.

A slight clearance between the inner sleeve upper edge 36 and the drivers 30 on the one hand ensures that the drivers 30 actually leave the inner sleeve 29 and on the other permits desired stroke path differences between the first and second operations.

In order to achieve an advantageous, significant reusability of parts, the operating trigger 22 can be released from the casing 15 through the application of a radially acting force, in that the detents 24 are pressed in the direction of the ram 14 to such an extent that they no longer engage behind the end ring 25. The operating trigger 22 can then be drawn off axially rearwards. The return spring 26 preferably fixed for this purpose to the base surface 35 of the operating trigger 22 is also drawn off rearwards.

The spray cylinder 11 can now be removed from the casing 15 and preferably the cap 16 is simultaneously removed. As soon as the ram 14 is no longer connected to the piston 12, it is also possible to extract the ram 14 from the spray cylinder and use it again. A spray cylinder 11 optionally provided with a cap 16 and sealing element 17 together with the piston 12 located therein and new medium to be discharged can now be placed in the casing 15. Following the production of a bias on return spring 26, the operating trigger 22 can now be inserted in the shaft 33 of the casing 15. As soon as the operating trigger 22 is again retained by the end ring 25, the ram 14 can be reinserted through the insertion opening 34 of the operating trigger 22. This procedure has the advantageous that the ram 14 is not moved excessively in the direction of the discharge channel 13 during the refitting of the operating trigger 22 to the shaft 33 which might lead to an unintentional discharge of part of the medium to be discharged prior to the first operation. For securing the apparatus against unintentional operation, it can also be advantageous to only insert the ram 14 through the insertion opening 34 into the casing 15 and spray cylinder 11 immediately prior to a further use of the apparatus, because without it an unintentional operation of the apparatus is impossible.

Figure 2:
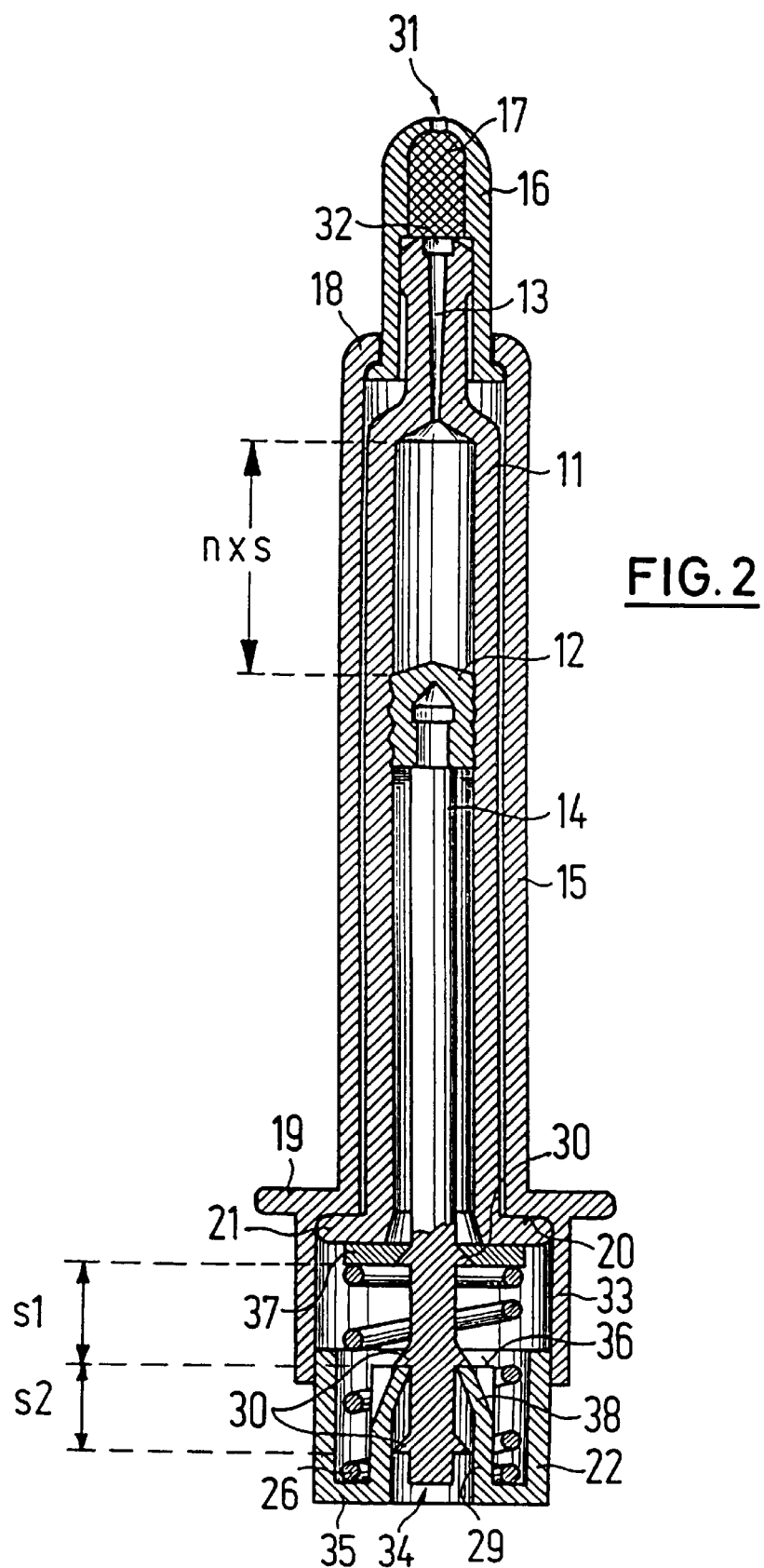
FIG. 2 The cross-section through a second embodiment with a limited operating path of an operating trigger.

FIG. 2 also shows a cross-section through an apparatus for the atomized discharge of an in particular medium. The medium is once again stored in the spray cylinder 11 in said apparatus. The spray cylinder issues into the discharge channel 13 with its opening 32, which is closed towards the nozzle 31 by the sealing element 17 placed in the cap 16. The cap 16 is held on the spray cylinder by the connecting edge 18 of the casing 15. The spray cylinder 11 is also guided in the casing 15. The piston 12 is axially displaceable located on the side of the spray cylinder 11 remote from discharge channel 13. The piston is manually operated by means of the ram 14 and the operating trigger 22. For applying a force to the operating trigger 22 the casing 15 has the finger bearing surface 19. The spray cylinder 11 is supported in the casing 15 with its widening 21 on the contact surface 20 of the casing 15. The locking disk 37 engages on the widening 21 of the spray cylinder 11. Between the locking disk 37 or widening 21 and the base surface of the operating trigger 22 is located the return spring 26 ensuring the return of the operating trigger 22 from the operation end position to the operation starting position shown. Once again the operating trigger 22 is cup-shaped and is guided in the shaft 33 and the casing 15. In the represented operation starting position the operating trigger 22 is so held on the shaft 33 by the not shown means that seen from the discharge channel 13, it cannot be moved away further rearwards. The cup-shaped operating trigger 22 has on its base surface 33 the insertion opening 34 though which the ram 14 can be introduced into the spray cylinder 11 in such a way that it engages on the piston 12. In this position the front drivers 30 engage on the locking disk 37. The push webs 38 of the inner sleeve 29 of the operating trigger 22 engage behind the next drivers 30, which are moved by length s of a partial stroke from the preceding drivers 30. In order to permit partial strokes s of differing magnitudes s1, s2 the drivers 30 can also have a spacing smaller than the length, but which must be greater than s/2, so that there is no engagement behind the one from the next driver 30. In this case during the idle path the push webs 38 slide along the ram 14 until the non-positive connection with the driver 30 of the corresponding discharge stroke is obtained. The magnitude of the second stroke s2 is smaller than the magnitude s1 of the first stroke. The inner sleeve 29 surrounds the insertion opening 34 and projects from the base surface 35 of the operating trigger 22 in the direction of the spray cylinder 11. The inner sleeve 29 has push webs 38 projecting into the movement space of the ram 14, but which are so elastic that during the return stroke of the operating trigger 22 they can be pushed so far radially outwards from the operation end position into the operation starting position that they can be moved over beyond the drivers 30 of the ram 14 and so free the movement space for the relative movement between shaft 14 and operating trigger 22 during the return stroke.

If the operating trigger 22 is operated, it is firstly necessary to apply a force such that the furthest forward driver 30, which engages on the locking disk 37, which forms a locking edge, reversibly spreads the locking disk 37 in such a way that the ram 14 can be moved into the spray cylinder 11. If this minimum operating force is exceeded, the shaft 14, moved by the push webs 38 of the operating trigger 22, is moved further into the spray cylinder 11 in the direction of the discharge channel 13 and thereby moves with it the piston 12 of the spray cylinder 11. This takes place until the upper edge of the operating trigger 22 facing the spray cylinder 11 engages on the widening 21 of the latter. In this position the first drivers 30 have moved into the spray cylinder 11, the second drivers 30 engage on the locking disk 37 and the return spring 26 is compressed. If the operating trigger 22 is now released, the return spring 26 ensures that it is again moved back into the represented operation starting position. The push webs 38 glide along the ram 14 until they are spread by the leading edge of the third driver 30 and can consequently be moved over and beyond the same. As soon as the push webs 38 are moved away over the drivers 30, they again engage on the ram 14 and engage behind the third drivers 30. The second drivers 30 are used for the second, and in the represented example, final partial stroke as locking means, which ensure the application of the necessary minimum operating force for the further partial stroke.

In the represented embodiment the drivers 30 are constructed as thickenings, i.e. as radial cross-sectional widenings of the ram 14. In the vicinity of the driver 30, the ram 14 has a frustum-shaped cross-section, the apex of the cone pointing in the direction of the piston 12 of the spray cylinder 11. The push webs 38 engage on the base surface of the frustum of the drivers 30 for force transmission to the ram 14.

In order to permit a larger number of partial strokes, it is merely necessary to extend the ram 14 rearwards and provide it with further drivers 30. It must be simultaneously possible for the piston 12 to cover a corresponding path in the spray cylinder 11.

EMBODIMENT ACCORDING TO FIG. 3

Figure 3:
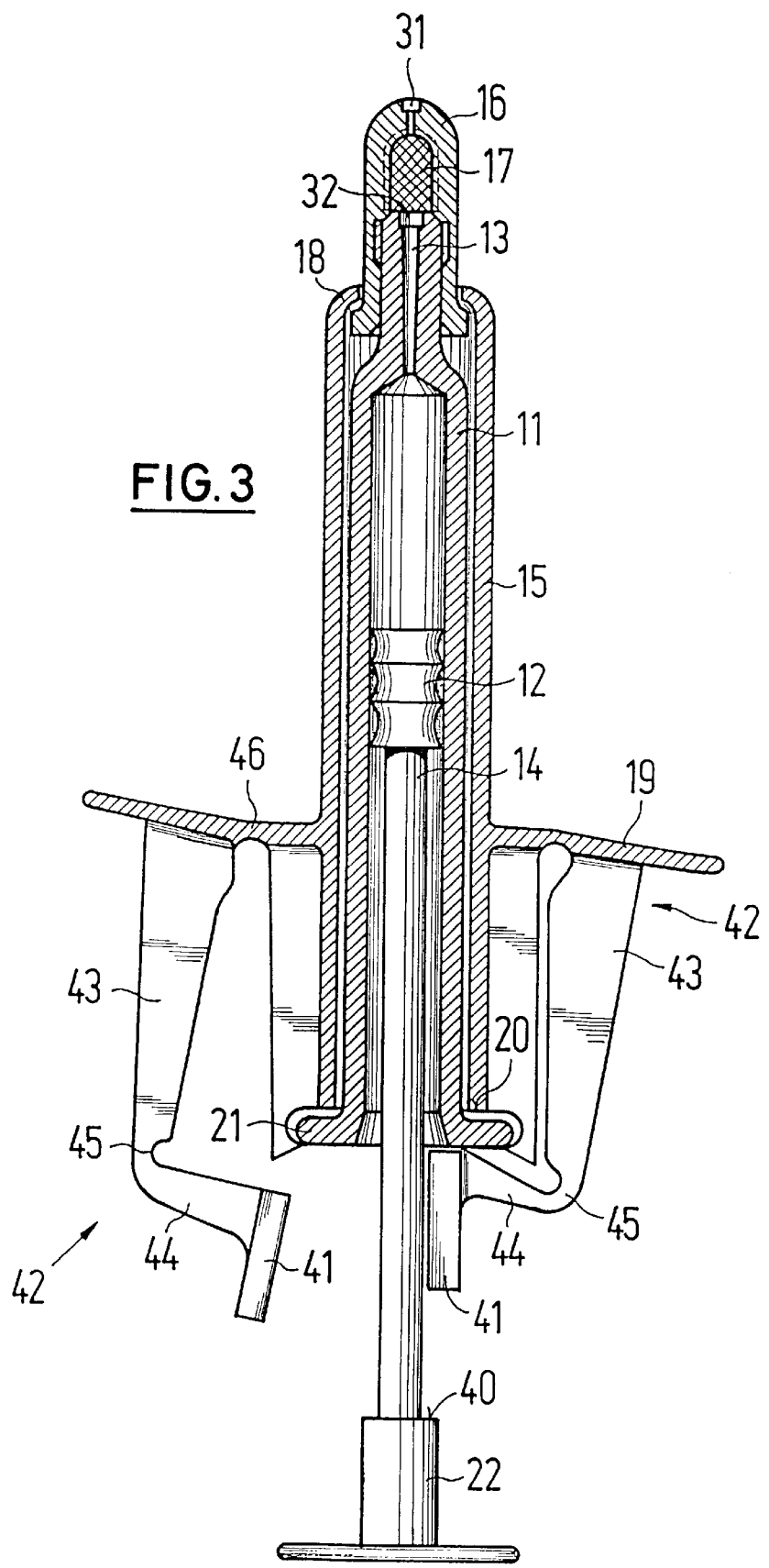
FIG. 3 The sectional representation of an embodiment in which the ram path is limited by sliding shoes engaging on the ram.

FIG. 3 is a cross-section of an apparatus for the optionally atomized discharge of an in particular liquid medium, in which the operating path of the spray cylinder piston is subdivided into partial strokes by sliding shoes.

At its front end a spray cylinder 11 has the discharge channel 13, which issues into the cap 16. The cap 16 has a nozzle 31 and the space between the nozzle 31 and the opening 32 of the discharge channel 13 is sealed by the sealing element 17. The spray cylinder 11 and cap 16 are held in the casing 15 by the connecting edge 18. The piston 12 is axially displaceably fitted in the spray cylinder 11. To the piston 12 is fixed the ram 14, which projects rearwardly out of the spray cylinder 11. The casing 15 extends over the length of the spray cylinder 11, so that the widening 21 of the spray cylinder 11 can be held in clamping manner on the contact surface 20 of casing 15.

The ram 14 shaped onto the piston 12 of the spray cylinder 11 has at its rear end remote from the piston 12 a collar 40, which is formed by a cross-sectional widening of the ram 14. The cross-sectional widening issues, in the case shown, into the operating trigger 22, which permits the application of an operating force by the user to the ram 14.

Laterally projecting finger bearing surfaces 19 are shaped on the casing 15. The finger bearing surface 19 has in its fixing area to the casing 15, which envelops the spray cylinder 11, a hinge, more particularly a film hinge 46. A lever 42 projects rearwards from the finger bearing surface 19, considered radially outside the film hinge. The lever 42 is formed from a first partial arm 43 extending substantially axially rearwards and a second partial arm 44, which is connected to the first partial arm 43 by means of a joint 45, particularly a film hinge, and has at its other end the sliding shoe 41.

The left-hand half of FIG. 3 shows the position occurring if no manual force is exerted on the finger bearing surface 19, whereas the right-hand half shows the case when a manual force acts on said surface 19.

According to the left-hand side of FIG. 3, the film hinge 46 and joint 45 are biased in such a way that the sliding shoe 41 does not engage on the ram 14 for as long as no force is applied to the finger bearing surface 19. This has the advantage that in simple manner the spray cylinder 11, optionally with the cap 16 fixed thereto, and the piston 12 with the ram 14, together with the operating trigger 22, are inserted prior to operation in the casing 15 and held therein by the shaping of the contact surface 20. It is then equally easy to remove the used spray cylinder 11 following the final partial stroke. The casing 15 together with the finger bearing surface 19 shaped thereon, as well as the levers 42 and sliding shoes 41, can be reused for numerous uses, whereas the spray cylinder 11 with cap 16, together with the piston 12, ram 14 and operating trigger 22 are only used once, e.g. for hygienic reasons.

If a finger is applied to the finger bearing surface 19 and consequently a force is applied, the said bearing surface 19 is pressed rearwards (from the side remote from the discharge channel 13) in the area radially outside the film hinge 46. The levers 42 with their first partial arms 43 and second partial arms 44 engage the sliding shoes 41 on the ram 14.

If the operating trigger is now operated, the sliding shoes slide along the ram 14 until the collar 40 engages on the sliding shoes 41 and a jamming or wedging takes place between collar 40, ram 14 and sliding shoes 41. This ensures that the ram 14 is not moved forwards in the direction of the discharge channel 13 further than the collar 40. The collar 40 comprises a cross-sectional widening of the ram 14. With the leading edge the sliding shoes 41, during jamming, preferably engage on the widening 21 of the spray cylinder 11, so that the sliding shoes are further supported. The biased joint 45 between the first partial arm 43 and the second partial arm 44 of the lever 42 acts as a spring which, after relieving the operating trigger 22, ensures that the sliding shoes are shoved axially over the collar 40 counter to the stroke direction. This ensures that there is no relocking on the same collar 40 when the operating trigger 22 is operated again. Through the multiple arrangement of a collar 40 on the ram 14, it is possible on the basis of this principle to produce several, clearly defined strokes. By means of different spacings between one collar 40 and a following collar 40, it is possible to obtain defined strokes of different magnitudes.

What is claimed is:

1. Apparatus for the atomized discharge of a medium, the medium being dischargeable by way of a discharge channel from a spray cylinder in which a piston is displaceably located, the piston being manually operable by means of a ram and the apparatus having an operating trigger which acts on the ram, the operating trigger having a movement along an operating path between an operation starting position and an operation end position, wherein the movement of the operating trigger (22) is limited in such a way that the discharge stroke of the piston (12) resulting from an operation of the operating trigger (22) is limited to the amount necessary for the discharge of a partial charge; and
    wherein the ram is formed with spaced apart drivers with spacings corresponding to partial strokes (s1, s2) for partial discharge of the medium;
    and wherein said spacings have different magnitudes corresponding to partial strokes of different magnitudes.

2. Apparatus according to claim 1, wherein a return spring (26) is positioned in such a way that the operating trigger is automatically returned to the operating starting position.

3. Apparatus according to claim 1, wherein drivers (30) provide a non-positive connection between the operating trigger (22) and ram (14) solely in the direction of the discharge stroke.

4. Apparatus according to claim 1, wherein the drivers (30) are constructed as thickenings of the ram.

5. Apparatus according to claim 1, wherein the drivers (30) are formed from frustum-shaped sections of the ram (14), each having an imaginary cone apex that points in the direction of the piston (12).

6. Apparatus according to claim 1, wherein the spray cylinder (11) is held in a casing (15).

7. Apparatus according to claim 6, wherein the casing (15) has finger bearing surfaces (19) for at least one finger.

8. Apparatus according to claim 7, wherein the operating trigger (22) is guided in the casing (15).

9. Apparatus according to claim 8, wherein the operating trigger (22) is detachably placed on the casing (15).

10. Apparatus according to claim 6, wherein the casing (15) has a bearing surface (20) on which can be engaged a widening (21) of the spray cylinder (11), so that the spray cylinder (11) is supported against the operating force of the ram (14).

11. Apparatus according to claim 10, wherein the widening (21) is formed on the end of the spray cylinder (11) remote from the discharge channel (13).

12. Apparatus according to claim 1, wherein the discharge channel issues into a cap (16), which has an outlet port, including a nozzle (31).

13. Apparatus according to claim 12, wherein the flow path between the discharge channel (13) and the outlet port is sealed by means of a sealing element (17).

14. Apparatus according to claim 13, wherein the flow path can be reversibly freed as a result of the medium pressure during the operation of the operating trigger (22).

15. Apparatus according to claim 14, wherein the flow path is irreversibly freed during the first operation of the operating trigger (22).

16. Apparatus according to claim 13, wherein the cap (16) and sealing element (17) are replaceable.

17. Apparatus according to one of the claim 12, wherein the cap (16) is fixed by a press fit to the discharge channel (13).

18. Apparatus according to claim 12, wherein the cap (16) is held in the casing, on a connecting edge (18).

19. Apparatus according to claim 1, wherein at least the spray cylinder (11) with its piston (12) is interchangeably held in the casing (15).

20. Apparatus according to claim 19, wherein additionally the ram (14) is replaceable.

21. Apparatus for the atomized discharge of a medium, the medium being dischargeable by way of a discharge channel from a spray cylinder in which a piston is displaceably located, the piston being manually operable by means of a ram and the apparatus having an operating trigger which acts on the ram, the operating trigger having a movement along an operating path between an operation starting position and an operation end position, wherein the movement of the operating trigger is limited in such a way that the discharge stroke of the piston resulting from an operation of the operating trigger is limited to the amount necessary for the discharge of a partial charge;

wherein the spray cylinder is held in the casing;

wherein the casing has a bearing surface on which can be engaged a widening of the spray cylinder, so that the spray cylinder is supported against the operating surface of the ram; and wherein a locking disc, on which a return spring is supported, rests on the widening.

22. Apparatus according to claim 21, wherein the locking disc (37) serves as a locking edge (28).

* * * * *

UNITED STATES PATENT AND TRADEMARK OFFICE
CERTIFICATE OF CORRECTION

PATENT NO. : 6,427,878 B1
DATED : August 6, 2002
INVENTOR(S) : Greiner-Perth et al.

It is certified that error appears in the above-identified patent and that said Letters Patent is hereby corrected as shown below:

Column 1,
Line 52, "one-hand-operation" should be -- one-hand operation -- (delete hyphen in "hand-operation")

Column 6,
Line 16, "s/2" should be -- s2 --

Column 8,
Line 41, "operating starting" should be -- operation starting --

Signed and Sealed this

First Day of July, 2003

JAMES E. ROGAN
*Director of the United States Patent and Trademark Office*